United States Patent [19]

Sekihara et al.

[11] Patent Number: 5,170,119
[45] Date of Patent: Dec. 8, 1992

[54] PROCESS AND APPARATUS FOR DETERMINING THE BIOCURRENT DISTRIBUTION OF A LIVING BODY WHEN THE EXACT NUMBER OF FIELD SOURCES IS NOT KNOWN

[75] Inventors: Kensuke Sekihara, Musashimurayama; Nagaaki Ohyama, Kawasaki; Hideaki Haneishi, Chiba; Toshio Honda, Yokohama, all of Japan

[73] Assignee: Hitachi, Ltd., Tokyo, Japan

[21] Appl. No.: 676,077

[22] Filed: Mar. 27, 1991

[30] Foreign Application Priority Data

Mar. 28, 1990 [JP] Japan ................................. 2-076883
Apr. 27, 1990 [JP] Japan ................................. 2-110013

[51] Int. Cl.$^5$ ........................ G01R 33/02; A61B 5/05
[52] U.S. Cl. ............................. 324/260; 364/413.01; 364/413.13; 364/571.02; 128/653.1
[58] Field of Search ............... 324/301, 248, 244, 260, 324/261; 505/842-846; 364/413.01, 413.02, 570, 571.01, 571.02, 571.05, 571, 08, 572-582, 413.13; 128/653.1

[56] References Cited

U.S. PATENT DOCUMENTS 4,486,835  12/1984  Bai et al. ............................. 364/414
4,771,239  9/1988  Hornig ................................ 324/248

FOREIGN PATENT DOCUMENTS 3725532  2/1989  Fed. Rep. of Germany.
307681  12/1989  Japan ................................. 324/248

OTHER PUBLICATIONS

Gudden et al, "Ein Vielkanalsystem zur Biomagnetischen Diagnostik in Neurologie und Kardiologie: Prinzip, Methode und erste Ergebnisse", (translated: A Multi-Channel System for Biomagnetic Diagnosis in Neurology and Cardiology; Principle, Method and First Results), 2332 *ElectroMedica*, vol. 57, No. 1, 1989 pp. 2-7.

Meiss et al, "The EEG and MEG, Using a Model of Eccentric Spheres to Describe the Head", *IEEE Trans. on Biomed. Eng.* vol. BME-34, No. 12, Dec. 1987, pp. 913-920.

Haneishi et al, "Analysis of the Cost Function used in Simulated Annealing for CT Image Reconstruction", *Applied Optics*, vol. 29, No. 2, Jan. 19, 1990, pp. 259-265.

Szu et al, "Fast Simulated Annealing", *Physics Letters A*, vol. 122, No. 34, Jun. 8, 1987, pp. 157-162.

*Primary Examiner*—Gerard R. Strecker
*Assistant Examiner*—Warren S. Edmonds
*Attorney, Agent, or Firm*—Antonelli, Terry, Stout & Kraus

[57] ABSTRACT

A process and an apparatus for measuring the biocurrent distribution call for initially assuming a number of multiple currents which is more than the number of isolated currents possibly existing in a living body and calculating the virtual magnetic field created by the assumed currents at actual measuring points. The estimated location and current vectors of said assumed currents are consecutively changed to decrease the difference between said virtual and actual magnetic fields so that the estimated location and current vectors of the assumed currents having the number corresponding to the true isolated currents substantially approximate the true values and the estimates of the other assumed currents approximate zero. This enables the biocurrent distribution to be exactly determined even when the number of isolated currents is not preliminarily known.

16 Claims, 2 Drawing Sheets

PROCESS AND APPARATUS FOR DETERMINING THE BIOCURRENT DISTRIBUTION OF A LIVING BODY WHEN THE EXACT NUMBER OF FIELD SOURCES IS NOT KNOWN

BACKGROUND OF THE INVENTION

The present invention relates to a process and an apparatus for measuring the biocurrent distribution and in particular to a process and an apparatus for indirectly determining the biocurrent distribution by measuring the biomagnetic field and estimating the distribution of the biocurrents which are sources of the magnetic field based upon the measured data.

Estimation of the biocurrent distribution from the measured values of the biomagnetic field is usually performed as follows:

Description will be made by way of a neuromagnetic measurement which is a typical biomagnetic field measurement.

The coordinate system is defined as shown in FIG. 1. It is assumed that a current represented as a vector $q_n$ exists at a position $r_n$ in the drawing. Such an isolated current vector can be assumed as far as the interface of the brain can be considered as a spherical surface in the field of neuromagnetic field measurement and this current vector will be referred to as a current dipole. A reference $r_m$ in FIG. 1 denotes the coordinate of the measuring point.

If it is assumed that N current dipoles exist in the brain, the magnetic flux density vector $B_m$ at point $r_m$ can be expressed from Biot-Savart's law as follows:

$$B_m = \sum_{n=1}^{N} \frac{\mu_0}{4\pi} \frac{q_n \times (r_m - r_n)}{|r_m - r_n|^3} \quad (1)$$

The magnetic field component which can be measured by a magnetometer is the component of $B_m$ normal to the surface of the brain. The actual value measured at $r_m$ is denoted as $D_m$.

If the estimated location and current vectors of each dipole are expressed by superscripting a reference mark ^, the virtual measured value $\hat{D}_m$ which is calculated from the estimates is expressed as follows:

$$\hat{D}_m = \sum_{n=1}^{N} \frac{\mu_0}{4\pi} \frac{\hat{q}_n \times (r_m - \hat{r}_n) \cdot r_m}{|r_m - \hat{r}_n|^3 |r_m|} \quad (2)$$

A cost function is herein defined as follows:

$$E(\hat{r}_1, \hat{r}_2, \ldots \hat{r}_N; \hat{q}_1, \hat{q}_2, \ldots \hat{q}_N) = \sum_{m=1}^{M} (D_m - \hat{D}_m)^2 \quad (3)$$

Equation (3) shows the degree of matching between estimated data and actually measured data.

Optimum estimated values have heretofore been determined as $\hat{r}_1, \ldots, \hat{r}_N, \ldots, \hat{q}_1, \ldots, \hat{q}_N$ which minimize the cost function defined by the equation (3).

It is found from the foregoing that the number N of the biomagnetic field sources, that is, the current dipoles should be known in order to carry out the conventional measuring method. In other words, the conventional method can be carried out only if the number of the current dipoles is known.

If N which is different from the number of actual current dipoles is preset and a solution of $\hat{r}_1, \ldots, \hat{r}_N$, $\hat{q}_1, \ldots, \hat{q}_N$ which minimizes the cost function is determined, the solution would then show a distribution different from the actual biocurrent distribution.

SUMMARY OF THE INVENTION

It is an object of the present invention to provide a process and an apparatus for measuring the biocurrent distribution of a living body to obtain a solution exactly showing the biocurrent distribution even if the number of the magnetic field sources, that is, the exact number of the current dipoles in a living body to be measured is not known.

In order to accomplish the above-mentioned object, in accordance with the present invention, multiple currents larger in number than the numbers of the isolated currents which are expected to exist in a living body are assumed, and a virtual magnetic field created by each assumed current at an actually measured point is calculated. The estimated location and current vectors of the assumed currents are changed to reduce the difference between the virtual magnetic field and the actual magnetic field for determining the optimum estimates. In this case, the absolute values of the excess assumed current vectors are approximated to zero.

If multiple isolated currents, for example, current dipoles larger in number than the number of currents actually existing are assumed and the estimates ar changed so that the matching between the distribution of the magnetic field calculated from the assumed current dipoles and the distribution of the actually measured magnetic field is enhanced, an excessive degree of freedom would be introduced. Accordingly, there is the high possibility that a solution,, different from the actual current distribution will be obtained. In other words, it is presumed that the magnetic field formed at the measuring point may be substantially equal to the magnetic field formed by the current dipole assumed as a true current dipole (refer to equation (1)), if the current vector of the current dipole which is assumed to be located at a position closer to the measuring point than the position of the true current dipole is smaller than the true current dipole.

Hence, in accordance with the present invention, a fact is considered that the assumed current dipoles are more than the true current dipoles in magnitude by the number of the assumed current dipoles over the number of true current vectors of the assumed current dipoles if the assumed current dipoles are compared with the true current dipoles in only the magnitude or the energy (for example, magnetic field) which they give.

That is, when optimum values of the estimated locations and current vectors of the currents are determined so that the difference between the magnetic field calculated from the assumed currents and the actual magnetic field becomes smaller, the excessive degree of freedom of the optimum values is restricted by decreasing the magnitude of the current dipoles or the energy that they give so that the optimum values of the current vectors of the assumed currents which are an excess over the number of the true currents approximate to zero.

In accordance with the present invention, an excessive freedom degree of freedom is restricted by using the total sum or the total sum of the $\alpha$-th power of the absolute values of the current vectors of the assumed current dipoles, or the total sum of the magnitudes of the magnetic fields, each formed solely by each assumed current dipole or the total sum of the α-th power of the magnitudes thereof.

BRIEF DESCRIPTION THE DRAWINGS

FIG. 1 a schematic view illustrating an embodiment of neuromagnetic field measuring of the present invention and the coordinate system used for estimation of; and FIGS. 2A and 2B are flow charts showing a process of simulated annealing of the present embodiment.

DESCRIPTION OF THE PREFERRED EMBODIMENTS

Embodiments of the present invention will be described with reference to a neuromagnetic field measurement.

Figure 1:
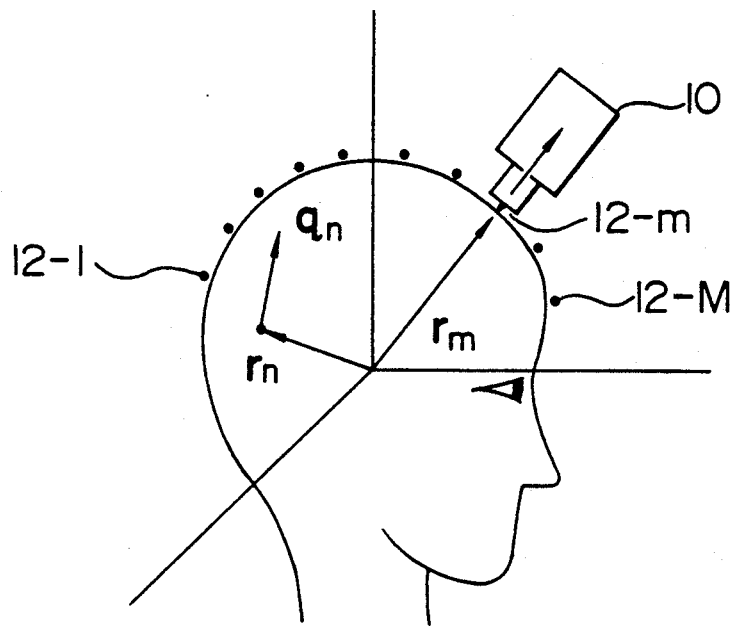

The neuromagnetic field measurement is conducted by measuring the component of the magnetic field in a direction normal to the brain 'surface at measuring points around a head while moving a magnetic flux meter 10 from points, 12-1 to 12-M as shown in FIG. 1. A presumption of the space coordinates and current vectors of current dipoles in the brain which are sources generating magnetic fields can be conducted based upon the measured values obtained at measuring points around the head to accordance with the present invention as follows:

The number of the measuring points on the surface of the head is assumed to be M and the measuring points are numbered from 1 to M. The position of the m-th measuring point is represented by a vector at position $r_m$. The measured value of the magnetic field at that point is represented as $D_m$.

It is assumed that N current dipoles are contained in the brain. The present invention is applicable to a case in which an exact number of the dipoles are not known. The selected value N is for a time preset to be larger than the number of the dipoles which are expected to exist in the brain.

The estimated location and current vectors of the thus assumed current dipoles are represented by $r_n$ and $\hat{q}_n$, respectively wherein n=1, 2, ..., N. The magnetic field $\hat{D}_m$ (m=1, 2, ..., M) which is created at the measuring points by the thus assumed current dipoles is determined by a calculation. That is, $\hat{D}_m$ can be referred to as the measured value of a virtual magnetic field determined from the assumed current dipoles. If the surface of the head is approximated by a spherical surface and the center of the sphere is assumed as an origin of the coordinates, $\hat{D}_m$ is calculated by an equation as follows:

$$\hat{D}_m = \sum_{n=1}^{N} \frac{\mu_0}{4\pi} \frac{\hat{q}_n \times (r_m - \hat{r}_n) \cdot r_m}{|r_m - r_n|^3 |r_m|} \quad (2)$$

By an optimization operation which will be described in detail, the estimated location and current vectors of the assumed current dipoles are changed so that a minimum value which the cost function assumes is determined. Following equation is used as the cost function in the present embodiment.

$$E(\hat{r}_1, \hat{r}_2, \ldots, \hat{r}_N, \hat{q}_1, \hat{q}_2, \ldots, \hat{q}_N) = \quad (4)$$
$$\sum_{m=1}^{M} (D_m - \hat{D}_m)^2 + Es(\hat{q}_1, \hat{q}_2, \ldots, \hat{q}_N)$$

The first term of the right formula of equation (4) denotes matching between the distribution of the actually measured magnetic field and the distribution of the magnetic field created by the assumed current dipoles. If the respective distributions are represented by row vectors, G and $\hat{G}$, the first term can be represented as $|G - \hat{G}|^2$ wherein $$G = \begin{pmatrix} D_1 \\ D_2 \\ \cdot \\ \cdot \\ \cdot \\ D_M \end{pmatrix} \hat{G} = \begin{pmatrix} \hat{D}_1 \\ \hat{D}_2 \\ \cdot \\ \cdot \\ \cdot \\ \hat{D}_M \end{pmatrix}$$

On the other hand, the second term in equation (4) is assumed as the sum total of the magnetic fields, each created by an individual assumed current dipole. The detailed form of Es ($q_1, q_2, \ldots, q_N$) is as follows:

$$Es(\hat{q}_1, \hat{q}_2, \ldots, \hat{q}_N) = w \sum_{n=1}^{N} |g_n| \quad (5)$$

wherein $$g_n = \begin{pmatrix} g_n^1 \\ g_n^2 \\ \cdot \\ \cdot \\ \cdot \\ g_n^M \end{pmatrix} \quad (6)$$

and $g_n^m$ is calculated as follows:

$$g_n^m = \frac{\mu_0}{4\pi} \frac{\hat{q} \times (r_m - \hat{r}_n) \cdot r_m}{|r_m - \hat{r}_n|^3 \cdot |r_m|} \quad (7)$$

The component $g^m_n$ in a direction normal to the surface of the brain (the component vertical to the face of a detecting coil) of the magnetic field created at the m-th measuring point by the n-th current dipole is calculated by equation (7) for each position m=1, 2, ..., M. The magnitude of the row vector $g_n$ having respective components, that is, the norm $|g_n|$ of the magnetic field created by the n-th current dipole is calculated. Specifically, the root of the sum of the square of the normal component of the magnetic field created by the n-th current dipole at each measuring point is calculated. The magnetic field $|q_n|$ individually created by each current dipole is determined in such a manner and the sum total with respect to n assumed current dipoles is determined to provide Es in equation (5).

Es ($\hat{q}_1, \ldots, \hat{q}_N$) represented by equation (5) serves to suppress the excessive degree of freedom introduced by assuming that the dipoles are more in number than the number of actually contained dipoles. Although it is hard to logically and exactly verify this in case of a non-linear inverse problem like the estimation of the magnetic field source in the brain, which in an object of the present invention, the linear inverse problem can be mathematically verified. This verification is discussed in H. Haneishi et al. "An analysis of cost function used in simulated annealing for CT image reconstruction", Applied Optics in Press.

"w" in equation (5) is a constant for weighting the first and second terms in the right expression of the equation (4). "w" is preset by preliminarily calculating Δ E as a trial so that the contribution is not biased to only one of the first and second terms in equation (4) when a change in the cost function ΔE is calculated for optimization operation which will be described hereafter.

Although equation (5) may be directly used as the term of Es in equation (4), it is more preferable to use a reformed equation as follows:

$$Es(\hat{q}_1, \hat{q}_2, \ldots, \hat{q}_N) = w \sum_{n=1}^{N} |q_n|^\alpha \quad (5')$$

wherein an index of power $\alpha$ is a positive real number.

The role of $\alpha$ in equation (5') is as follows:

The true current distribution is estimated by assuming that the current dipoles are more in number than the number of the current dipoles which are expected to exist in the brain, in accordance with invention. Accordingly, there is the possibility that a plurality of current dipoles are estimated in substantially the same position. $\alpha$ in the equation (5') determines the nature of the solution obtained in such a case. A case in which two current dipoles u-th and v-th are estimated in substantially the same position, that is, a case in which $\hat{r}_u \doteq \hat{r}_v$ will now be exemplarily described.

(1) In case of $0 < \alpha < 1$, either one of the current vectors $q_u$ and $q_v$ of the u-th and v-th current dipoles becomes very small. That is, $|\hat{q}_u| \doteq 0$ or $|\hat{q}_v| \doteq 0$. In other words, one current vector of a plurality of current vectors having interposed space coordinates approximates the current vector of a current dipole which inherently exists in that position and the magnitudes of the current vectors of the other current dipoles become substantially zero.

(2) In case or $\alpha > 1$, $\hat{q}_u \doteq \hat{q}_v$. These values are about a half of the value of the current vector of the current dipole which inherently exists in position $r_u \doteq r_v$.

(3) In case of $\alpha = 1$, a value $\hat{q}_u + \hat{q}_v$ approximates a current vector value of the curren the dipole which exists in position $r_u \doteq r_v$. Which value a ratio $|\hat{q}_u|$ to $|\hat{q}_v|$ assumes cannot be predicted.

Briefly, it is preferable that $\alpha$ be other than 1, and $0 < \alpha < 1$ is most preferable (for example, $\alpha = \frac{1}{2}$).

An optimization operation which determines estimates $\hat{r}_n$, $\hat{q}_n (n=1, \ldots, N)$ for making minimum the cost function E ($\hat{r}_1, \ldots, \hat{r}_N; \hat{q}_1, \ldots, \hat{q}_N$) defined by equation (4), more specifically equation (5) or (5') will be described in detail. The cost function E is non-linear with respect to the variable and has a localized minimum value. Accordingly, it is impossible to determine a true minimum value (a global minimum value) by known non-linear optimization approaches. The present embodiment adopts a recently proposed simulated annealing method which can determine a global minimum value even in such a case.

Figure 2B:
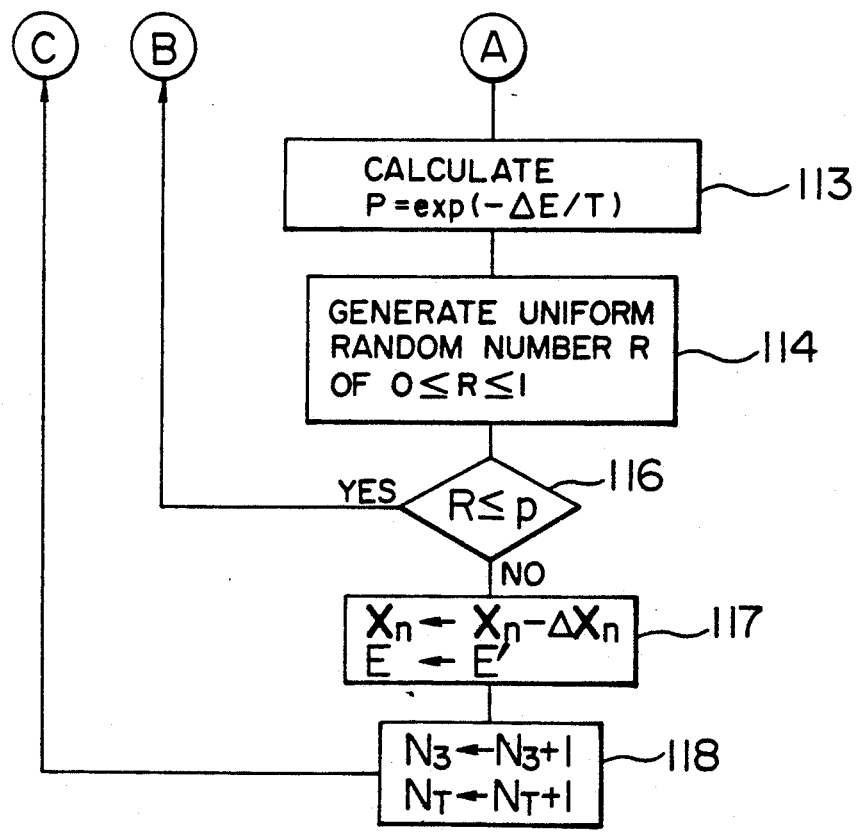

This method will now be described with reference to FIGS. 2 A and B.

The above-mentioned N current dipoles are assumed and a proper value is preset as an initial value for each respective coordinate $r_n$ (n=1, . . . , N) and current vector $q_n$ (n=1, . . . , N) is preset as a variable $X_n$ (n=1, 2 . . . , N) and the current vector $q_n$ (n=1, 2, . . . , N) of each current dipole is preset as a variable $X_n$ (n=N+1, N+2, . . . , 2N). The values of the cost function E which has been described in detail are calculated by using the actually measured and recorded values $D_m$ (m=1, . . . , M) of the magnetic field (step 101).

Thereafter, the value of $X_n$ is changed by a very small amount (this is referred to as trial). Whether or not the trial is accepted is determined with reference to a change ΔE which in the cost function E occurred as a result of the trial. The value of each $X_n$ is gradually approximated to the true value.

Firstly, a sufficiently high parameter T is preset. The parameter T determines the probability that the change is accepted even if ΔE >0, and is referred to as temperature.

ΔE is calculated by a trial calculation and T is preset so that exp $(-\Delta E/T) = 0.8$ to 0.9. The changes $|\Delta \hat{r}|$ and $|\Delta \hat{q}|$ in one trial are preset for variables $\hat{r}_1, \ldots, \hat{r}_N$ and $\hat{q}_1, \hat{q}_2, \ldots, \hat{q}_N$, respectively. (step 102)

It is adequate that the value of $|\Delta \hat{r}|$ be about 1 mm to 10 mm and the value of $|\Delta \hat{q}|$ be about 1/10 to 1/1000 of a predicted maximum value of $|\hat{q}|$.

Then, respective initial values zero are preset for parameters $N_T$, $N_1$, $N_2$ for repeated control of the trial operation (step 103).

One variable $X_n$ which will be an object of the trial is then chosen (step 106) to determine a change in vector $\Delta X_n$ (step 107). If the variable $X_n$ is a coordinate, the following equations are used.

$$(\Delta x_n)_X = |\Delta \hat{r}| \sin \theta \cos \psi$$
$$(\Delta x_n)_Y = |\Delta \hat{r}| \sin \theta \cos \psi \quad (8)$$
$$(\Delta x_n)_Z = |\Delta \hat{r}| \cos \theta$$

If the variable $X_n$ is a current vector, the following equations are used.

$$(\Delta x_n)_X = |\Delta \hat{q}| \sin \theta \cos \psi$$
$$(\Delta x_n)_Y = |\Delta \hat{q}| \sin \theta \cos \psi \quad (9)$$
$$(\Delta x_n)_Z = |\Delta \hat{q}| \cos \theta$$

The change in vector is determined by generating uniform random numbers $\theta$ and $\psi$ in the ranges of $0 \leq \theta < 2\pi$ and $0 \leq \psi \pi$, respectively.

The variable $X_n$ is replaced with $X_n + \Delta X_n$ in step 108. In other words, a trial is executed.

In step 109, the difference ΔE between previous and subsequent cost functions E which give a change $\Delta X_n$ is calculated as follows:

$$\Delta E = E(x_1, \ldots, x_n + \Delta x_n, \ldots, x_{2N}) - E(x_1, \ldots, x_n, \ldots, x_{2N}) \quad (10)$$

If ΔE <0, the change $\Delta X_n$ is then accepted in step 111. That is, calculation program is returned to step 106 for trial of next variable $X_{n+1}$ via steps 112 and 105 while $X_n + \Delta X_n$ is taken as $X_n$. If ΔE >0, whether the change $\Delta X_n$ is accepted or refused is determined according to a probability P(ΔE) =exp $(-\Delta E/T)$ depending upon temperature as shown in steps 113, 114 and 116. If it is determined that the change is accepted, the calculation program returns to step 106 via steps 115 and 105 while taking $X_n + \Delta X_n$ as new $X_n$. If the change is determined to be refused, $X_n$ and the cost function E are returned to original values in step 117 and the program is returned to step 106 via steps 118 and 105.

Such a series of steps are executed for each variable, that is, for n =1 through 2N. This operation is repeated a total of $N_T^{max}$ times. It is adequate that, for example, a value of about 100 to 400 is adequate as $N_T^{max}$.

Figure 2A:
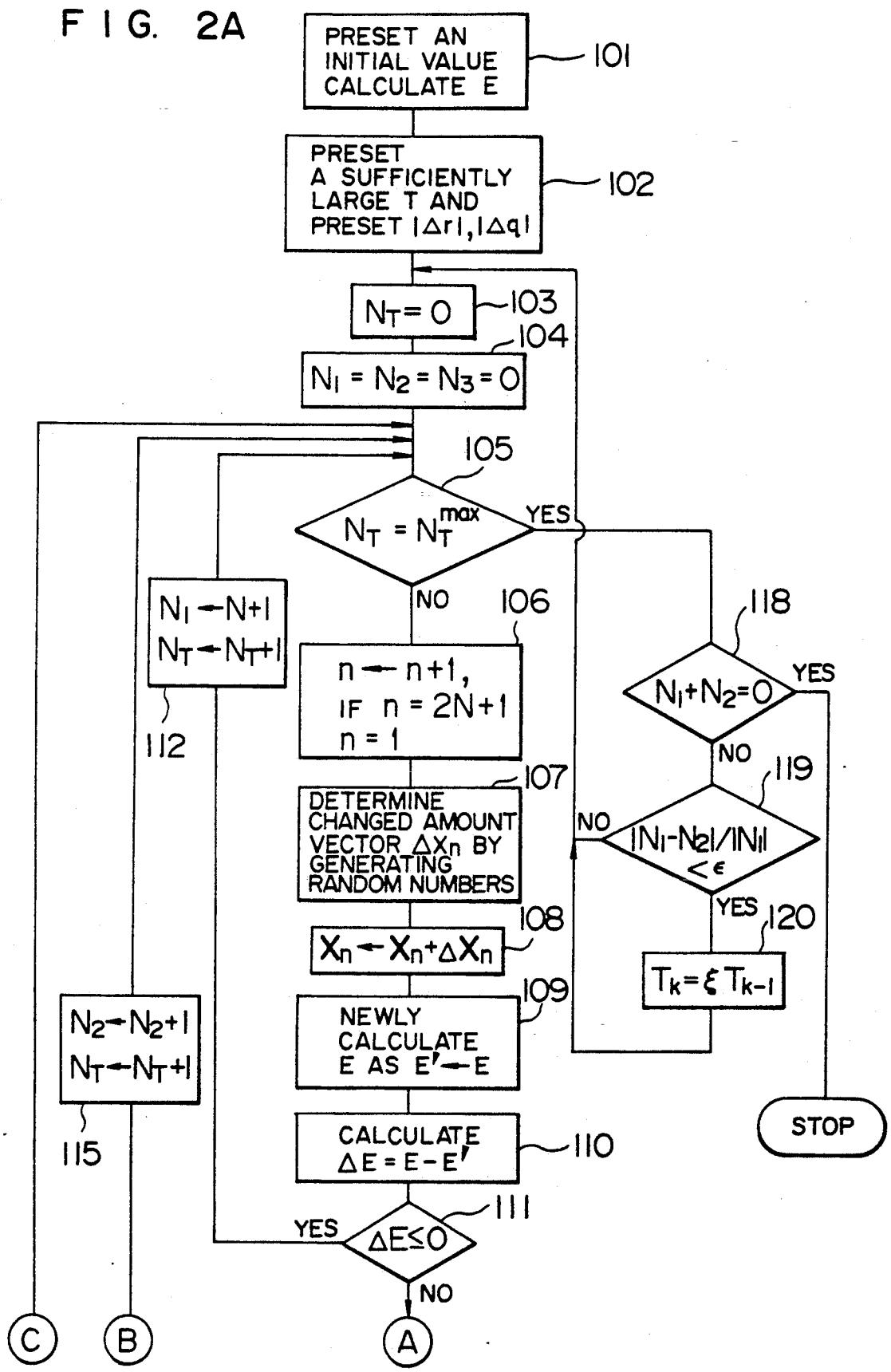

$N_1$ in step 112 of a flow chart of FIG. 2A denotes a number of changes accepted in such a direction that the cost function is decreased, $N_2$ in step 115 denotes the number of changes accepted in such a direction that the cost function is increased. $N_3$ in step 105 denotes the number of the refused changes. When it is found in step 105 that $N_T^{max}$ trials are completed, the program proceeds to a step at which determination of whether or not the temperature T determining the probability of acceptance of change is lowered is performed. That is, it is determined based on a value of $|N_1 - N_2|$ whether or not the number $N_1$ of increases of the cost function of the accepted trials approximates the number of decreases of the cost function. If this value is not less than $\epsilon$ (for example, about 0.02), the program is returned to step 103 without changing the temperature and trials will be repeated $N_T^{max}$ times. If the value of $|N_1 - N_2|/N$ is lower than $\epsilon$, the program proceeds to step 120. By lowering the temperature T, the probability that the change to make $\Delta E > 0$ is accepted is decreased and thereafter the program proceeds to step 103 and the trials are similarly repeated $N_T^{max}$ times.

An approach to make $T_k = \xi T_{k-1}$, as a k-th temperature step is adopted in the present embodiment to lower the temperature T in step 120. A value of about 0.9 through 0.95 is used as $\xi$ at this time. Another approach to lower the temperature by $T_k = T_o/(1+k)$ or $T_k = T_o/\log(e+k)$ is also proposed in a publication Vol. 122, p157, 1987 (H. Szu et al., "Fast Simulated Annealing", Physics Letters A, Vol. 122, p157, 1987).

As $N_T^{max}$ trials of changes of each variable and are repeated in some cycles while gradually lowering the temperature T, as mentioned above, each variable approximates an optimum value and the accepted change is gradually decreased. When it is determined that $N_1 + N_2 = 0$, in step 118, that is, there is no accepted change of the tried changes, a variable which minimizes the cost function, that is, optimum location and current vectors of a current dipole are obtained. Therefore, the simulated annealing operation is ended.

Although the present embodiment has been described with reference to a case in which simulated annealing is used for an optimization operation, the present invention is not limited- to this case. The other algorithms which can determine a true minimum value from a function containing a localized minimum value, such as the Genetic Algorithm proposed by J. H. Holland can be used.

If areas at which dipoles exist are a priory known in advance, the priory information can be incorporated into the optimization operation as follows:

In this case, each estimate which minimizes E which is calculated by the following equation (11) in lieu of equation (4) is determined.

$$E(\hat{r}_1, \hat{r}_2, \ldots, \hat{r}_N; \hat{q}_1, \hat{q}_2, \ldots, \hat{q}_N) = \sum_{m=1}^{M} (D_m - \hat{D}_m)^2 + Es(\hat{q}_1, \ldots, \hat{q}_N) + E_L(\hat{r}_1, \ldots, \hat{r}_N) \quad (11)$$

$E_L$ is defined as follows:

1) If all $\hat{r}_1, \ldots, \hat{r}_N$ exist in preliminarily preset areas, $E_L(\hat{r}_1, \ldots, \hat{r}_N) = 0$ 2) If any of $\hat{r}_1, \ldots, \hat{r}_N$ moves out of the preliminarily preset areas, $E_L(\hat{r}_1, \ldots, \hat{r}_N) = \Lambda$ wherein is a value which is sufficiently high for the current temperature $T_1$ that is, such a value that $\exp(-\Lambda/T) \doteq 0$.

By defining $E_L$ in such a manner, the probability that a change by which each $\hat{r}_n$ moves out of the preliminarily preset area is accepted is approximately zero. An estimate which minimizes $$E(\hat{r}_1, \ldots, \hat{r}_N; \hat{q}_1, \ldots, \hat{q}_N) = \sum_{m=1}^{M} (D_m - \hat{D}_m)^2 + Es(\hat{q}_1, \ldots, \hat{q}_N)$$

can be determined in preliminarily preset area.

Although a case has been described in which the second amount expressed by equation (5) or (5'), that is, the magnetic field created by the assumed current dipole is used as the second term of equation (4) for restricting the degree of freedom, equation (5'') of the total sum of absolute values of current vectors of the presumed current dipoles or equation (5''') of the $\alpha$-th power of the total sum may be used in lieu of equation (5) or (5').

$$Es(\hat{q}_1, \hat{q}_2, \ldots, \hat{q}_N) = w \sum_{n=1}^{N} |q_n| \quad (5'')$$

$$Es(\hat{q}_1, \hat{q}_2, \ldots, \hat{q}_N) = w \sum_{n=1}^{N} |q_n|^\alpha \quad (5''')$$

In equation (5'') and 5'''), the meaning of w and $\alpha$ are sames as those of equations (5) and (5').

Since terms of position vectors are included in equations (5) and (5''), the degree of freedom is more restricted than in equations (5'') and (5''').

We claim:

1. A process to be performed by a computer for determining the distribution of biocurrents in a living body by measuring the biomagnetic field generated by the activity of the living body at a plurality of measuring points using a magnetometer to indirectly determine the distribution of the isolated currents in said living body from plural measured values of the magnetic field detected by the magnetometer, comprising the steps of:
   (a) measuring the actual magnetic field at each of said measuring points using said magnetometer;
   (b) selecting a number of assumed multiple currents which exceeds the number of said isolated currents possible existing in said living body so as to preset estimated locations and current vectors of the assumed multiple currents;
   (c) calculating a virtual magnetic field of each measuring point from the estimated locations and current vectors of the assumed multiple currents using said computer; and
   (d) consecutively changing the estimated locations and current vectors of said assumed multiple currents using said computer so as to decrease the difference between said virtual and actual magnetic fields, until vector of the assumed currents having a number corresponding to the true isolated currents substantially approximate the true values and the estimates of the other assumed currents approximate zero.

2. A process for determining the biocurrent distribution, as defined in claim 1, in which said step includes the steps of:
   (d1) changing said estimated location and current vectors;
   (d2) calculating a first amount representative of the difference between said virtual and actual magnetic fields;

(d3) calculating a second amount from each of said estimated current vectors; and (d4) determining said estimated location and current vectors from said first and second amounts.

3. A process for determining the biocurrent distribution, as defined in claim 2, in which said step (d4) of determining said estimated location and current vectors includes presetting a cost function including at least said first and second amounts and determining the estimated location and current vectors by using the cost function.

4. A process for determining the biocurrent distribution, as defined in claim 3, in which said cost function includes a linear sum of said first and second amounts.

5. A process for determining the biocurrent distribution, as defined in claim 4, in which said step of determining said estimated location and current vectors is executed by minimizing the cost function.

6. A process for determining the biocurrent distribution, as defined in claim 4, in which said second amount is the total sum of the absolute values of said estimated current vectors.

7. A process for determining the biocurrent distribution, as defined in claim 4, in which said second amount is the total sum of the $\alpha$-the power ($\alpha$ is a positive real number) of the absolute values of said estimated current vectors.

8. A process for determining the biocurrent distribution, as defined in claim 7, in which $\alpha \neq 1$.

9. A process for determining the biocurrent distribution, as defined in claim 7, in which $0 < \alpha 1$.

10. A process for determining the biocurrent distribution, as defined in claim 5, in which said second amount is the total sum of the absolute values of the magnetic fields, each created at each measuring point by each of said assumed current vectors.

11. A process for determining the biocurrent distribution, as defined in claim 4, in which said second amount is the total sum of the absolute values of the magnetic field's components normal to the surface of said living body, each magnetic field being created by each of said assumed current vector at each measuring point.

12. A process for determining the biocurrent distribution, as defined in claim 4, in which said second amount is the total sum of $\alpha$-th power ($\alpha$ is a positive real number) of absolute values of the magnetic field's components normal to the surface of said living body, each magnetic field being created by each of said assumed current vector at each measuring point.

13. A process for determining the biocurrent distribution, as defined in claim 12, in which $\alpha \neq 1$.

14. A process for determining the biocurrent distribution, as defined in claim 12, in which $0 < \alpha < 1$.

15. A process for determining the biocurrent distribution, as defined in claim 5, in which said step of determining said estimated location and the current vectors includes a first step of accepting a change in said estimates executed in the step of changing said estimates when said cost function decreases, and a second step of accepting a change in said estimates in a probability relating to a given temperature even when said cost function increases.

16. An apparatus for determining the biocurrent distribution in a living body by measuring the magnetic field generated by the activity of the living body at a plurality of measuring points to indirectly determine the distribution of isolated currents in the living body from the plural measured values of the magnetic field, comprising:

means for measuring the actual magnetic field at said measuring points; and a computer including:

(i) means for inputting a number representing assumed multiple currents, which inputted number exceeds the number of said isolated currents possibly existing in said living body, and for presetting an estimated location and current vector for each assumed current;

(ii) means for calculating a virtual magnetic field at each measuring point from the estimated locations and current vectors; and (iii) means for consecutively changing the estimated locations and current vectors of said assumed currents to decrease the difference between said virtual and actual magnetic fields, until the estimated locations and current vectors of the assumed currents having a number corresponding to the true isolated currents substantially approximate the true values and the estimates of the other assumed currents approximate zero.

* * * * *